United States Patent [19]

Masson

[11] Patent Number: 5,192,577
[45] Date of Patent: Mar. 9, 1993

[54] NUTRITIONAL COMPOSITION AND A PROCESS FOR ITS PRODUCTION

[75] Inventor: Gérard Masson, Cully, Switzerland

[73] Assignee: Nestec S.A., Vevey, Switzerland

[21] Appl. No.: 763,411

[22] Filed: Sep. 20, 1991

[30] Foreign Application Priority Data

Oct. 26, 1990 [CH] Switzerland .......................... 3430/90

[51] Int. Cl.$^5$ ............................................. A23D 7/00
[52] U.S. Cl. .................................... 426/602; 426/656; 426/658; 514/938
[58] Field of Search ............... 426/602, 607, 800, 801, 426/658, 656; 514/938

[56] References Cited

U.S. PATENT DOCUMENTS 3,697,287 10/1972 Wünitz .
4,497,800 2/1985 Larson et al. ............................ 514/2

OTHER PUBLICATIONS

Graham, Food Colloids, 1977, pp. 347-381, 506, 507, 514 and 515.
Fennema, Food Chemistry 1985, p. 175.

Primary Examiner—Joseph Golian
Assistant Examiner—Evan Federman
Attorney, Agent, or Firm—Vogt & O'Donnell

[57] ABSTRACT

A nutritional composition in the form of an oil-in-water emulsion containing an amino acid source and a glucide is stabilized by the presence of a combination of kappa-carrageenan and xanthan gum. The composition is prepared by mixing a colloidal solution containing an amino acid source and a glucide with an oil-in-water emulsion. The stabilizers may be incorporated into the composition by adding them to the colloidal solution prior to mixing the solution with the emulsion or by adding them after mixing the colloidal solution with the emulsion. The composition also may be sterilized.

22 Claims, No Drawings

NUTRITIONAL COMPOSITION AND A PROCESS FOR ITS PRODUCTION

BACKGROUND OF THE INVENTION

This invention relates to a nutritional composition in the form of an oil-in-water emulsion which can be sterilized and taken enterally and to a process for its production.

U.S. Pat. No. 3,697,287, for example, relates to the preparation of food compositions which are capable of supplying the essential nutritive elements required by the human body and which contain amino acids and/or an amino acid source, such as proteins, glucides and lipids, and an emulsifier and, optionally, vitamins and mineral salts. Although these compositions have a high nutritive value and may be used as a supplement or replacement product for food products in human beings in good health, they are primarily intended for the pre-operational and/or post-operational treatment of patients, or even in patients with digestion problems. Since the compositions are generally intended for enteral administration, particularly by means of a nasogastric probe, it is important that they should be present in homogeneous and stable form. Now, one of the main problems presented by these compositions is their inability to form aqueous emulsions showing prolonged stability, particularly after sterilization, even with the aid of an emulsifier.

A solution to this problem is proposed in U.S. Pat. No. 4,497,800 and comprises forming an emulsion which, in addition to a protein source, lipids and glucides, contains a stabilizer consisting of a particular mixture of diacetyl tartrate, mono- and diglycerides and carrageenan. The emulsion thus formed is then sterilized, for example for about 10 seconds at 90° to 140° C., and is capable of retaining its physical and nutritive qualities over a prolonged period. However, one disadvantage of this process lies in the use of synthetic stabilizers.

SUMMARY OF THE INVENTION

The problem addressed by the present invention was to produce on an industrial scale a composition which would have a high nutritive content and which would retain its properties of physical and chemical stability and also nutritional stability for prolonged periods, even after sterilization, without synthetic stabilizers having to be used. By physical stability is meant a composition of apparently homogeneous structure and texture which does not cream, flocculate, sediment, coagulate, form serum or discolour after storage for prolonged periods at ambient temperature.

Accordingly, the present invention relates to a nutritional composition in the form of an oil-in-water emulsion which, per part, contains at least $0.6 \cdot 10^{-3}$ part kappa-carrageenan and at least $0.1 \cdot 10^{-3}$ part xanthan gum.

The present invention also relates to a process for the production of this nutritional composition in which an oil-in-water emulsion is prepared, a colloidal solution containing an amino acid source and a glucide source is prepared, a kappa-carrageenan and a xanthan gum are added to the colloidal solution to obtain a final nutritional composition containing per part at least $0.6 \cdot 10^{-3}$ part kappa-carrageenan and at least $0.1 \cdot 10^{-3}$ part xanthan gum, after which the emulsion and the colloidal solution are mixed.

Finally, the present invention relates to a process for the production of the nutritional composition in which an oil-in-water emulsion is prepared, a colloidal solution containing an amino acid source and a glucide source is prepared, the emulsion and the colloidal solution are mixed and a kappa-carrageenan and a xanthan gum are added to the resulting mixture to obtain a final nutritional composition containing per part at least $0.6 \cdot 10^{-3}$ part kappa-carrageenan and at least $0.1 \cdot 10^{-3}$ xanthan gum.

The composition thus prepared may then be sterilized and packed under aseptic conditions The composition may also be packed first and then sterilized. The emulsion and the colloidal solution may also be separately sterilized before mixing and then mixed and packed under aseptic conditions.

DETAILED DESCRIPTION OF THE INVENTION

In the following description, parts and percentages are by weight.

To carry out the processes according to the invention, an oil-in-water emulsion is prepared, consisting of a mixture of an aqueous phase and a lipid phase.

The lipid phase may be formed by edible oils of vegetable origin, such as palm oil, olive oil and sunflower oil, or of animal origin, such as butter oil, or by a mixture of these various oils, oils rich in polyunsaturated fatty acids being preferred. Fat-soluble vitamins, such as vitamins A, D, E and K, may be added to the lipid phase along with lecithins emanating, for example, from egg or soya. The aqueous phase is formed mainly by water, preferably distilled or demineralized water, to which glucides may be added.

It has been found that, to keep the stability of the final nutritional composition correct, it is preferable for the osmolalities of the oil-in-water emulsion and the colloidal solution to be very similar so as to obtain a final composition of which the osmolality is preferably between 250 and 1,000 mOsm/kg. In the context of the present invention, osmolality is understood to be the number of osmotically active mols per kilogram of product taken as reference, in the present case per kilogram of water (unit Osm/kg water). The desired total quantity of glucides in the final nutritional composition is thus distributed between the aqueous phase of the emulsion and the colloidal solution to keep the osmolalities of these two solutions close and thus to strengthen the stability of the final composition.

To prepare the oil-in-water emulsion while improving its physico-chemical stability, the aqueous and lipid phases may be separately heated with continuous stirring to a temperature of 40° to 55° C., preferably in an inert gas atmosphere, for example nitrogen, to avoid possible contamination or oxidation of the fats. The two phases may then be mixed, for example by addition of 10 to 45 parts lipid phase to 100 parts aqueous phase, again with continuous stirring and at a temperature of 40° to 55° C.

To improve the stability of the emulsion obtained, the size of the droplets of the lipid phase may be reduced, for example by homogenization. To this end, the emulsion may be pre-homogenized under a pressure of 15 to 25 bar to obtain an average droplet size of the order of 1.5 to 2.5 $\mu$m and then homogenized, for example in a homogenizer under a high pressure of the order of 200 to 800 bar. This particular step may be repeated several times to obtain an emulsion of which the average droplet size in the lipid phase is of the order of 0.15 to 0.35 μm. The homogenization is preferably carried out at 40° to 55° C. The homogenized emulsion is then stirred continuously in an inert gas, such as nitrogen. After homogenization, the emulsion is left to cool to ambient temperature and then neutralized, for example by addition of sodium hydroxide, to a pH of 7 to 7.4.

A colloidal solution containing an amino acid source and a glucide source may be prepared at the same time as the emulsion. In one particular embodiment, a first aqueous solution containing the amino acid source, a second aqueous solution containing the glucide source and, optionally, a third aqueous solution containing vitamins and mineral salts are prepared and the various solutions thus prepared are then mixed. The colloidal solution thus contains an amino acid source, preferably in solution in distilled or demineralized water.

The amino acid source may be formed by amino acids, peptides, denatured or hydrolyzed proteins or by a mixture of these various compounds. The colloidal solution also contains a glucide source. These glucides may be mono- or polysaccharides, such as sucrose, maltose, frustose or glucose, maltodextrins having a dextrose equivalent of 10 to 50 and preferably around 45, polyalcohols or a mixture of these various compounds. The quantity of glucides added to the colloidal solution is dependent on the quantity of glucides present in the emulsion, as mentioned above. Mineral salts, vitamins and/or oligoelements, preferably in aqueous solution, may then be added to the colloidal solution. Flavourings may also be added to the colloidal solution.

The nutritional composition according to the invention is distinguished in particular by the fact that it contains per part at least $0.6 \cdot 10^{-3}$ part kappa-carrageenan and at east $0.1 \cdot 10^{-3}$ xanthan gum.

Carrageenan is a polysaccharide consisting of a complex mixture of polymers, including kappa-carrageenan, corresponding to the formula:

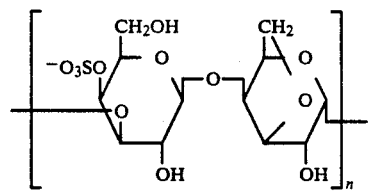

Xanthan gum is a polysaccharide consisting of a cellulose chain to which oligosaccharides are attached and corresponds to the following formula:

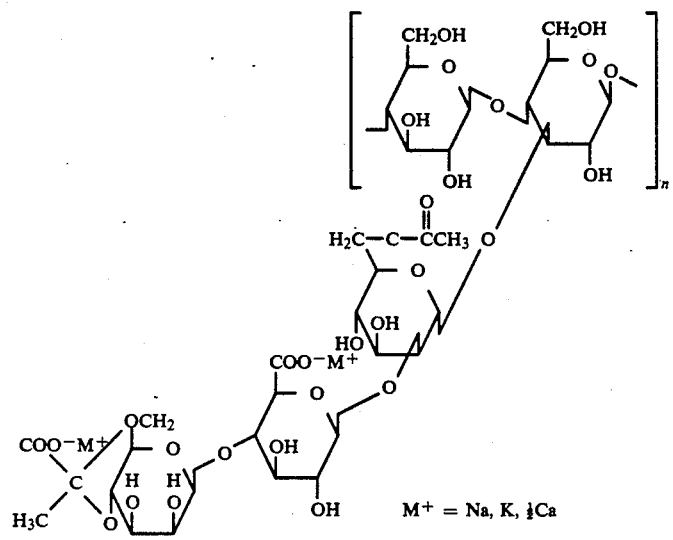

It has been found that the presence of these constituents in a composition in the form of an oil-in-water emulsion provides the composition with good physical stability, even when it contains significant quantities of amino acids, for example, and/or when it is subsequently sterilized. In the present case, the addition of these constituents to the colloidal solution or to the mixture of the emulsion and the colloidal solution enables the physical stability of the final composition to be improved by providing it with non-newtonian and rheofluidifying behaviour. It is possible that these particular constituents improve the steric stability of the composition by trapping the lipid droplets in a network consisting of peptide chains and molecules of the polysaccharides kappa-carrageenan and xanthan gum.

Kappa-carrageenan and xanthan gum are thus added to obtain a final composition containing per part at least $0.6 \cdot 10^{-3}$ part kappa-carrageenan and at least $0.1 \cdot 10^{-3}$ part xanthan gum. In a preferred embodiment, no more than $1 \cdot 10^{-3}$ part of each constituent per part final composition is added in order to provide the final composition with a suitable viscosity. These constituents are preferably added in aqueous solution either together or one after the other. For example, they may be added to the colloidal solution before it is mixed with the emulsion. They may also be added to the mixture formed by the emulsion and the colloidal solution.

The mixture preferably contains 10 to 45% oil-in-water emulsion of pH 7-7.4 and 55 to 90% colloidal solution of pH 6.7-8.7. The composition thus obtained has a physiologically acceptable pH value and a correct viscosity which allows flow and administration of the composition, preferably a viscosity of the order of 30 to 50 mPa.s (shear rate 50 s$^{-1}$).

In one particular embodiment for the preparation of a sterilized composition, the emulsion and the colloidal solution containing the kappa-carrageenan and the xanthan gum may first be mixed, for example while heating to 40° to 50° C. in an inert gas and then continuously stirring the resulting mixture for about 30 minutes to homogenize the composition formed. The composition may then be sterilized, for example by UHT treatment, and packed under aseptic conditions in cans, cartons or bottles. The composition may also first be packed in cans, cartons or bottles and then suitably sterilized.

In another particular embodiment for the preparation of the composition according to the invention, the emulsion and the colloidal solution may first be separately sterilized, for example by UHT treatment, subsequently mixed under aseptic conditions and, finally, packed either aseptically or semi-aseptically which necessitates subsequent sterilization of the cans, cartons or bottles.

The nutritional composition thus obtained is in the form of an emulsion which retains its stability for long periods.

The nutritional composition is preferably in the form of an oil-in-water emulsion which contains per part amino acid source from 0.5 to 7.5 parts of a glucide source and from 0.4 to 1.2 parts of a lipid source which has a dry matter content of 12 to 38% and which additionally contains per part at least 0.6·10$^{-3}$ part kappa-carrageenan and at least 0.1·10$^{-3}$ part xanthan gum.

EXAMPLES

The invention is illustrated in more detail by the following Examples in which the measurements are carried out as follows:

1) Measurement of viscosity

Viscosity is measured with a VOR Bohlin rheometer under the following conditions:

| | |
|---|---|
| measuring system | C.14 cylinder |
| torsion bar | 0.24 g.cm and 19.8 g.cm |
| initial holding time | 60 s |
| measuring time | 20 s at constant deformation |
| integration time | 10 s |
| shear rate | 50 s$^{-1}$ or 150 s$^{-1}$ |

2) Measurement of osmolality

Osmolality is measured with a Roebling osmometer by measurement of the cryoscopic fall of the solution using pure water as reference.

3) Measurement of the fats content

The fats content of the composition is determined by measuring the quantity of lipids as follows:
a precise quantity of 10 to 20 g of liquid to analyzed is removed;
this liquid is diluted with 20 ml of a 10% aqueous NaCl solution;
the pH is adjusted to 3 by addition of a 0.1 N aqueous HCl solution;
the lipids are extracted four times with 50 ml of a solution containing 3 parts N-hexane and 2 parts isopropanol;
the organic phase obtained is washed with 30 ml 10% NaCl and the aqueous phase obtained is washed with 30 ml N-hexane; and
the organic phases are combined and dried over anhydrous sodium sulfate and then filtered.

The organic solvents are then evaporated under reduced pressure, and the quantity of lipids is obtained by weighing. The content T of fats, expressed in %, is obtained by ratioing the weighed quantity of lipids and the quantity of liquid initially removed.

4) Determination of physical stability

In order quantitatively to characterize the physical stability of the nutritional compositions prepared, their stability index (SI) is determined as follows:
a first sample of the composition prepared is taken and its fats content T 1 is determined;
a second sample is taken and centrifuged at 1,000 r.p.m. for 15 minutes at 25° C.;
separation into two more or less distinct phases generally occurs; the fats content T 2 of the lower part of the centrifuged sample is determined; and
the stability index SI (in %) is obtained by forming the ratio $$\frac{T2 \times 100}{T1}$$

Example 1

An oil-in-water emulsion is prepared by mixing an aqueous phase containing 20 g sucrose dissolved in 100 ml demineralized water and a lipid phase containing 6.5 g corn oil, 9.5 g lactic fats, 16 g medium-chain triglycerides and 2.0 g soya lecithin. The two phases are preheated to 45°-50° C. and are mixed under nitrogen with continuous stirring.

The emulsion thus formed is pre-homogenized in a suitable apparatus for about 30 minutes under a pressure of 20 bar and at a temperature of 50° C. to obtain droplets of lipid phase having an average size of the order of 1.5 to 2.5 μm. The prehomogenized emulsion is then introduced into a two-stage homogenizer, in which the total pressure is approximately 500 bar, at a temperature of 50° C.

This step may be repeated several times until the droplets of lipid phase have an average size of the order of 0.2 to 0.3 μm.

The emulsion is then neutralized to pH 7.4 by addition of a 0.5 N aqueous sodium hydroxide solution.

At the same time, a first solution containing 47 g maltodextrin (DE 11), kappa-carrageenan and xanthan gum as stabilizers in the proportions indicated below and 270 ml demineralized water is prepared.

A second solution containing 30 g denatured lactalbumin and 470 ml demineralized water is also prepared This solution may be heated for a few minutes to 50°-80° C. to facilitate dissolution of the proteins.

Finally, a third solution containing approximately 4.0 g of a balanced mixture of mineral salts containing calcium, magnesium, sodium and potassium ions in 25 ml demineralized water is prepared.

The three solutions thus prepared are mixed under nitrogen and stirring at a constant speed is continued while the colloidal solution formed is gently heated for 30 minutes to a temperature of approximately 45° C. to enable the stabilizers to perform their function completely.

The emulsion preheated to 45° C., and having an osmolality of 605 mOsm/kg, is then added to the colloidal solution, having an osmolality of 243 mOsm/kg and a pH of 6.7, in a nitrogen atmosphere with stirring at 750 r.p.m. for 30 minutes at the temperature of 45° C.

The nutritional composition obtained has a dry matter content of 13 to 14% and is then sterilized by UHT treatment for 3-5 seconds at 140° to 145° C. and then packed under aseptic conditions in bottles.

Depending on the quantities of kappa-carrageenan and xanthan gum present in the final composition, the following viscosity, osmolality and pH values are measured at 20° C. on the sterilized composition 15 hours after its preparation:

| Kappa-carrageenan (g) | 0.25 | 0.50 | 0.60 | 0.75 | 1.0 |
|---|---|---|---|---|---|
| Xanthan gum (g) | 0.75 | 0.50 | 0.40 | 0.25 | 1.0 |
| Viscosity at 50 $s^{-1}$ (mPa.s) | 32 | 15 | 55 | 55 | 116 |
| Viscosity at 150 $s^{-1}$ (mPa.s) | 18 | 9.5 | 33 | 28 | 55 |
| pH | 6.1 | 6.1 | 6.6 | 6.1 | 6.3 |
| Osmolality (mOsm/kg) | 320 | 312 | 293 | 301 | 304 |

The nutritional compositions thus prepared remain stable and show no signs of phase separation after storage for 15 h at ambient temperature (22°-25° C.).

Example 1A (Comparison)

A nutritional composition containing the following ingredients is similarly prepared for comparison:

| Composition A: | 1.0 g xanthan gum |
| | 0 g kappa-carrageenan |
| Composition B: | 0 g xanthan gum |
| | 1.0 g kappa-carrageenan |
| Composition C: | 1.0 g xanthan gum |
| | 1.0 g of a mixture of iota, lambda, mu and nu-carrageenan |

After preparation of the compositions and before sterilization, separation of the aqueous and lipid phases is observed for the three above-mentioned compositions A, B and C.

Accordingly, if the nutritional composition is to remain stable for at least 15 hours, even after sterilization, it must contain at least one xanthan gum and a kappa-carrageenan.

Example 1B

In order to quantify the physical stability of the compositions prepared, their stability index SI is determined. The following results are obtained:

| Kappa-carrageenan (g) | 0.25 | 0.50 | 0.60 | 0.75 | 1.0 |
|---|---|---|---|---|---|
| Xanthan gum (g) | 0.75 | 0.50 | 0.40 | 0.25 | 1.0 |
| SI (%) | 10 | 13 | 7 | 96 | 100 |

Separation of the aqueous and lipid phases is observed after sterilization for the first three compositions whereas the last two remain stable. The physical stability of these last two compositions is confirmed when they are stored for 27 weeks at 22°-25° C., during which no sign of phase separation is observed.

Example 2

Two compositions containing 0.75 g kappa-carrageenan and 0.25 g xanthan gum are prepared similarly to Example 1. To prepare the first composition (A), the kappa-carrageenan and the xanthan gum are added in aqueous solution to the colloidal solution after which the colloidal solution and the emulsion are mixed. To prepare the second composition (B), the kappa-carrageenan and the xanthan gum are added in aqueous solution to the emulsion and the emulsion and the colloidal solution are then mixed. The following results are obtained:

| | Composition | |
|---|---|---|
| | A | B |
| Viscosity at 50 $s^{-1}$ (mPa.s) | 55 | 48 |
| Viscosity at 150 $s^{-1}$ (mPa.s) | 28 | 29 |
| pH | 6.1 | 6.6 |
| Osmolality (mOsm/kg) | 301 | 303 |
| Stability index (%) | 96 | 5 |

Irreversible separation of the aqueous and lipid phases is observed for composition B whereas composition A remains stable for at least 15 hours, even after sterilization.

Example 3

An emulsion is prepared by mixing a lipid phase containing 15 g medium-chain triglycerides, 5.0 g rapeseed oil, 1.0 g soya lecithin and approx. 0.03 g fat-soluble vitamins A, D, E and K and 75 ml demineralized water containing 20 g sucrose in a nitrogen atmosphere at a temperature of 45° C.

The emulsion is homogenized in the same way as in Example 1 and then neutralized to pH 7.4. The emulsion is then sterilized by UHT treatment for 3-5 seconds at 140 to 145° C.

At the same time, a colloidal solution is prepared by mixing a first solution at 45° C. containing 42 g essential amino acids, principally leucine, isoleucine, valine, lysine and arginine, 1.0 g vitamins, including vitamins C and PP, and 300 ml demineralized water and a second solution at 45° C. containing 275 g maltodextrin (DE 50), kappa-carrageenan and xanthan gum in the quantities indicated below, 15 g mineral salts containing Ca, Mg, K, Na and P in ionic form and 250 ml demineralized water.

The colloidal solution thus formed is stirred at a constant speed for 30 minutes at 45° C. and then sterilized by UHT treatment for 3-5 seconds at 140°-145° C.

The sterilized colloidal solution having a pH of 8.6 and an osmolality of 1,500 mOsm/kg is then added under aseptic conditions to the sterilized emulsion having an osmolality of 605 mOsm/kg in a nitrogen atmosphere with stirring at 750 r.p.m. for 30 minutes at the temperature of 45° C.

The stable and sterilized nutritional composition obtained has a dry matter content of 37 to 38%;and the following characteristics measured at 20° C. on the sterilized composition after storage for 15 h at ambient temperature:

| Kappa-carrageenan (g) | 0.25 | 0.50 | 0.75 | 1.0 |
|---|---|---|---|---|
| Xanthan gum (g) | 0.75 | 0.50 | 0.25 | 1.0 |
| Viscosity at 50 $s^{-1}$ (mPa.s) | 40 | 47 | 58 | 144 |
| Viscosity at 150 $s^{-1}$ (mPa.s) | 25 | 30 | 35 | 76 |

| pH | 8.8 | 8.7 | 8.8 | 8.8 |
| --- | --- | --- | --- | --- |
| Osmolality (mOsm/kg) | 960 | 960 | 960 | 960 |

It can be seen that, in this case, the osmolality of the final composition is relatively high, on the order of 960 mOsm/kg, which is due to the fact that the composition contains a large number of osmotically active particles.

Determination of the stability index of the compositions thus prepared gives the following results:

| Kappa-carrageenan (g) | 0.25 | 0.50 | 0.75 | 1.0 |
| --- | --- | --- | --- | --- |
| Xanthan gum (g) | 0.75 | 0.50 | 0.25 | 1.0 |
| SI (%) | 45 | 24 | 16 | 88 |

Example 4

An emulsion is prepared by mixing an aqueous phase containing 35 g maltodextrin (DE 11) and 250 ml demineralized water and a lipid phase containing 15 g of a mixture of palm oil, coconut oil and safflower oil and 1.0 g soya lecithin. The emulsion is homogenized as in Example 1 and then neutralized to pH 7.4. The emulsion is then sterilized by UHT treatment for 3-5 seconds at 140°-145° C.

At the same time, the colloidal solution is prepared by mixing 60 g hydrolyzed lactalbumin permeate, 2.0 g mineral salts, kappa-carrageenan and xanthan gum as indicated below and 640 ml demineralized water. The colloidal solution is stirred for 30 minutes at 45° C. and then sterilized by UHT treatment for 3-5 seconds at 140°-145° C.

The emulsion having an osmolality of 357 mOsm/kg is then added under aseptic conditions to the colloidal solution having a pH of 6.9 and an osmolality of 294 mOsm/kg with stirring at 750 r.p.m. for 30 minutes at the temperature of 45° C.

The nutritional composition may be semi-aseptically packed and the bottles may then be post-sterilized for about 1 minute at 120°-122° C.

The stable and sterilized nutritional composition obtained has a dry matter content of 12-13% and the following characteristics measured at 20° C. on the sterilized composition after storage at 15 h at ambient temperature:

| Kappa-carrageenan (g) | 0.25 | 0.50 | 0.75 | 1.0 |
| --- | --- | --- | --- | --- |
| Xanthan gum (g) | 0.75 | 0.50 | 0.25 | 1.0 |
| Viscosity at 50 s$^{-1}$ (mPa.s) | 20 | 35 | 58 | 120 |
| Viscosity at 150 s$^{-1}$ (mPa.s) | 12 | 19 | 30 | 56 |
| pH | 6.2 | 6.1 | 6.0 | 6.3 |
| Osmolality (mOsm/kg) | 329 | 358 | 360 | 334 |
| SI (%) | 5 | 5 | 45 | 97 |

After sterilization, the first two compositions show separation of the aqueous and lipid phases whereas the last two compositions remain stable after sterilization for at least 27 weeks at 22° to 25° C.

Example 5

Five compositions are prepared in the same way as in Example 4, the kappa-carrageenan and the xanthan gum being added as follows:

| Composition A: | 0.75 g kappa-carrageenan and |
| --- | --- |
| | 0.25 g xanthan gum in aqueous solution are added to the colloidal solution. |
| Composition B: | 0.75 g kappa-carrageenan and 0.25 g xanthan gum in aqueous solution are added to the mixture formed by the colloidal solution and the emulsion. |
| Composition C: | 1.0 g kappa-carrageenan and 1.0 g xanthan gum in aqueous solution are added to the colloidal solution. |
| Composition D: | 1.0 g kappa-carrageenan and 1.0 g xanthan gum in aqueous solution are added to the mixture formed by the colloidal solution and the emulsion. |
| Composition E: | 1.0 g kappa-carrageenan and 1.0 g xanthan gum in solid form are added to the mixture formed by the colloidal solution and the emulsion. |

The compositions are sterilized for 30 minutes at 121° C. Slight separation of the aqueous and lipid phases is observed for some of the compositions, but disappears if the composition is gently stirred after its preparation. The following characteristics are measured at 20° C. after storage for 15 h at ambient temperature:

| | Composition | | | | |
| --- | --- | --- | --- | --- | --- |
| Xanthan gum (g) | A | B | C | D | E |
| Viscosity at 50 s$^{-1}$ (mPa.s) | 58 | 50 | 120 | 101 | — |
| Viscosity at 150 s$^{-1}$ (mPa.s) | 30 | 30 | 56 | 54 | — |
| pH | 6.0 | 6.7 | 6.3 | 6.7 | 6.6 |
| Osmolality (mOsm/kg) | 360 | 330 | 334 | 333 | 340 |
| SI (%) | 45 | 94 | 97 | 100 | 17 |

It can thus be seen that the kappa-carrageenan and the xanthan gum may be added either to the colloidal solution or to the mixture of the solution and the emulsion. In addition, the kappa-carrageenan and the xanthan gum are preferably added in the form of an aqueous solution.

Accordingly, the preceding Examples show that it is possible to obtain a sterilized and stable nutritional composition having an acceptable viscosity, pH and osmolality by adding at least $0.6 \cdot 10^{-3}$ part kappa-carrageenan and at least $0.1 \cdot 10^{-3}$ xanthan gum per part of the composition, and the same applying for various types of compositions.

I claim:

1. A process for preparation of a nutritional composition comprising preparing an oil-in-water emulsion, preparing a colloidal solution containing an amino acid source and a glucide, adding kappa-carrageenan and a xanthan gum to the colloidal solution and then mixing the emulsion and colloidal solution to obtain the nutritional composition, wherein the kappa-carrageenan and xanthan gum are added to the colloidal solution in amount so that the composition contains per part at least $0.6 \cdot 10^{-3}$ part kappa-carrageenan and at least $0.1 \cdot 10^{-3}$ part xanthan gum by weight.

2. A process for preparation of nutritional composition comprising preparing an oil-in-water emulsion, preparing a colloidal solution containing an amino acid source and a glucide, mixing the emulsion and colloidal solution to obtain an emulsion mixture to provide a nutritional composition, adding kappa-carrageenan and xanthan gum to the nutritional composition in amounts so that the composition contains per part at least 0.6·10⁻³ kappa-carrageenan and at least 0.1·10⁻³ xanthan gum by weight.

3. A process according to claim 1 or 2 wherein the emulsion has a pH of from 7 to 7.4 and the colloidal solution has a pH of from 6.7 to 8.7.

4. A process according to claim 11 wherein the composition contains 10% to 45% emulsion and 55% to 90% colloidal solution by weight.

5. A process according to claim 4 wherein the composition contains per part amino acid source from 0.5 to 7.5 parts glucide and from 0.4 to 1.2 parts lipid source and has a dry matter content of from 12% to 38% by weight.

6. A process according to claim 3 further comprising sterilizing the composition.

7. A process according to claim 1 or 2 wherein the emulsion contains fat-soluble vitamins and a glucide.

8. A process according to claim 7 wherein the colloidal solution contains vitamins and mineral salts.

9. A process according to claim 11 or 12 further comprising sterilizing the composition to obtain a sterile composition.

10. A process according to claim 9 further comprising packing the sterile composition under aseptic conditions.

11. A process according to claim 1 further comprising, prior to mixing the emulsion and colloidal solution containing the kappa-carrageenan and xanthan gum, sterilizing the emulsion and sterilizing the colloidal solution to obtain a sterile emulsion and solution and then mixing the sterile emulsion and solution under aseptic conditions.

12. A process according to claim 1 or 2 further comprising homogenizing the oil and water emulsion prior to mixing the emulsion with the colloidal solution.

13. The product of the process of claim 3.

14. The product of the process of claim 4.

15. The product of the process of claim 5.

16. The product of the process of claim 6.

17. A nutritional composition comprising an oil-in-water emulsion containing an amino acid source, a glucide and at least $0.6 \cdot 10^{-3}$ part kappa-carrageenan and at least $0.1 \cdot 10^{31\ 3}$ part xanthan gum per part of the composition by weight.

18. A composition according to claim 17 wherein the composition contains from $0.6 \cdot 10^{-3}$ part to $1 \cdot 10^{-3}$ part kappa-carrageenan and from $0.1 \cdot 10^{-3}$ part $1 \cdot 10^3$ part xanthan gum by weight.

19. A composition according to claim 17 or 18 wherein the composition contains 1 part of the amino acid source, from 0.5 to 7.5 parts of the glucide, and from 0.4 to 1.2 parts of a lipid source and has a dry matter content of from 12% to 38% by weight.

20. A composition according to claim 17 wherein the composition has an osmolality of between 250 mOsm/kg and 1,000 mOsm/kg.

21. A composition according to claim 17 wherein the composition is sterile.

22. A composition according to claim 17 wherein the composition does not contain a synthetic stabilizer.

* * * * *

UNITED STATES PATENT AND TRADEMARK OFFICE
CERTIFICATE OF CORRECTION

PATENT NO. : 5,192,577
DATED : March 9, 1993
INVENTOR(S) : Gerard MASSON, et al.

It is certified that error appears in the above-identified patent and that said Letters Patent is hereby corrected as shown below:

Column 2, between lines 36 and 37, insert the following paragraph:

--The glucides are selected from a group consisting of mono- or polysaccharides, such as sucrose, maltose, fructose or glucose, maltodextrins having a dextrose equivalent (DE) of 10 to 50, and preferably close to 45, and polyalcohols, such as glycerol, sorbitol or xylitol.--

Column 11, line 6, (line 1 of claim 4), "11" should be --3--.

Column 11, line 21, (line 1 of claim 9), "11 or 12" should be --1 or 2--.

Column 12, line 13, (line 4 of claim 17), "$10^{3/3}$" should be --$10^{-3}$--.

Signed and Sealed this

Sixteenth Day of November, 1993

Attest:

BRUCE LEHMAN

Attesting Officer     Commissioner of Patents and Trademarks